US00PP12626P2

(12) United States Plant Patent
Bryant

(10) Patent No.: US PP12,626 P2
(45) Date of Patent: May 14, 2002

(54) DIEFFENBACHIA PLANT NAMED 'BRYANT COMPACTA'

(76) Inventor: Theo Bryant, 7665 Crewsville Rd., Zolfo Springs, FL (US) 33890

( * ) Notice: Subject to any disclaimer, the term of this patent is extended or adjusted under 35 U.S.C. 154(b) by 0 days.

(21) Appl. No.: 09/561,018

(22) Filed: Apr. 28, 2000

(51) Int. Cl.[7] ..... A01H 5/00
(52) U.S. Cl. ..... Plt./378

(58) Field of Search ..... Plt./378

*Primary Examiner*—Bruce R. Campell
*Assistant Examiner*—W C Baker
(74) *Attorney, Agent, or Firm*—C. A. Whealy

(57) ABSTRACT

A distinct cultivar of Dieffenbachia plant named 'Bryant Compacta', characterized by its upright and outwardly arching growth habit; very freely clumping habit, full and dense plants, with typically about 20 offshoots per plant; and numerous and relatively small leaves with distinct green and light green and white variegated patterns.

3 Drawing Sheets

BACKGROUND OF THE INVENTION

The present Invention relates to a new and distinct cultivar of Dieffenbachia plant, botanically known as *Dieffenbachia amoena* and referred to by the cultivar name Bryant Compacta.

The new Dieffenbachia is a naturally-occurring whole plant mutation of an unnamed selection of *Dieffenbachia amoena*, not patented. The new Dieffenbachia was discovered by the Inventor in 1996 in a controlled environment in Zolfo Springs, Fla., as a single plant within a large population of plants of the unnamed selection of *Dieffenbachia amoena*.

The selection of this plant was based on its dense clumping habit with numerous offshoots and relatively small leaves. Compared to plants of the parent selection, plants of the new Dieffenbachia produce about 10 times as many offshoots per plant, are more compact, are more densely-foliate, and have smaller leaves. In addition, because of its dense compact growth habit, plants of the new Dieffenbachia maintain their size and shape under interior conditions much longer than plants of the parent selection.

Asexual propagation of the new cultivar by cuttings and by tissue-culture of meristem tips at Zolfo Springs, Fla., has shown that the unique features of this new Dieffenbachia are stable and reproduced true to type in successive generations.

SUMMARY OF THE INVENTION

The following traits have been repeatedly observed and are determined to be the unique characteristics of 'Bryant Compacta'. These characteristics in combination distinguish 'Bryant Compacta' as a new and distinct cultivar:

1. Upright and outwardly arching growth habit.

2. Very freely clumping habit, full and dense plants, with typically about 20 offshoots per plant.

3. Numerous and relatively small leaves with distinct green and light green and white variegated patterns.

Plants of the new Dieffenbachia can be compared to plants of the *Dieffenbachia amoena* cultivar Tropic Snow, not patented. However in side-by-side comparisons conducted by the Inventor in Zolfo Springs, Fla., plants of the new Dieffenbachia differed from plants of the cultivar Tropic Snow in the following characteristics:

1. Plants of the new Dieffenbachia are freely-clumping producing many offshoots per plant whereas plants of the cultivar Tropic Snow typically do not develop offshoots.

2. Because of its freely clumping habit, containers are planted with only one plant liner of the new Dieffenbachia whereas containers are typically planted with three plant liners of the cultivar Tropic Snow.

3. Plants of the new Dieffenbachia are much more dense with more leaves per plant than plants of the cultivar Tropic Snow.

4. Plants of the new Dieffenbachia have smaller leaves than plants of the cultivar Tropic Snow.

5. Leaves of plants of the new Dieffenbachia have proportionally more green to light green/white coloration than leaves of plants of the cultivar Tropic Snow.

The cultivar Bryant Compacta has not been observed under all possible environmental conditions. The phenotype may vary somewhat with variations in environment such as temperature, light intensity and/or fertilizer rate, without, however, any variance in genotype.

BRIEF DESCRIPTION OF THE PHOTOGRAPHS

The accompanying colored photographs illustrate the overall appearance of the new Dieffenbachia, showing the colors as true as it is reasonably possible to obtain in colored reproductions of this type. Colors in the photographs may differ slightly from the color values cited in the detailed botanical description which more accurately describe the actual colors of the new Dieffenbachia.

The photograph on the first sheet comprises a side perspective view of a typical plant of 'Bryant Compacta'.

The photograph on the second sheet comprises a side-by-side view of typical plants of the parent selection (left) and 'Bryant Compacta' (right).

The photograph at the top of the third sheet comprises a side-by-side view of the bases of typical plants of the parent selection (left) and 'Bryant Compacta' (right).

The photograph at the bottom of the third sheet comprises a side-by-side view of typical leaves of the parent selection (left) and 'Bryant Compacta'.

DETAILED BOTANIAL DESCRIPTION

The following observations, measurements and values describe plants of the new Dieffenbachia grown in 25-cm containers, in Zolfo Springs, Fla., in a polypropylene-covered shade house with day temperatures ranging form 16 to 35° C., night temperatures ranging from 10 to 27° C., and light levels ranging from 2,000 to 3,000 foot-candles. Plants used for this description were tissue-cultured liners that had been grown in the containers for about twelve months. Color references are made to The Royal Horticultural Society Colour Chart except where general terms of ordinary dictionary significance are used.

Botanical classification: *Dieffenbachia amoena* cultivar Bryant Compacta.

Parentage: Naturally-occurring whole plant mutation of an unnamed selection of *Dieffenbachia amoena*, not patented.

Propagation:

*Type.*—By cuttings.

*Time to initiate roots.*—Summer: About 14 days at 32° C. Winter: About 21 days at 21° C.

*Time to produce a rooted liner.*—Summer: About 70 days at 32° C. Winter: About 84 days at 21° C.

*Rooting description.*—Thick, white fleshy roots.

Plant description:

*Appearance.*—Upright and outwardly arching.

*Plant height.*—About 75 cm.

*Plant width.*—About 100 cm.

*Growth rate/vigor.*—Moderate.

*Crop time.*—From a tissue-cultured liner, about six months are required to produce a finished plant in a 15-cm container. From a tissue-cultured liner, about twelve months are required to produce a finished plant in a 25-cm container.

*Stem color.*—Close to 146A.

*Branching habit.*—Very freely clumping habit; tissue-cultured plants typically produce 20 offshoots per plant. Very full and dense plants.

*Foliage description.*—Densely foliated. Length: About 30 cm. Width: About 12 cm. Shape: Oblong to elliptical. Apex: Acute. Base: Obtuse. Margin: Entire. Aspect: Sightly concave to flat. Texture: Smooth. Midrib: Prominent on the lower surface. Primary veins: Recessed on upper surface and prominent on lower surface. Color: Dark green with light green and white chevrons radiating from the midrib. Upper surface: Shiny. Background: More green and lighter than 147A. Chevrons: 144A, 145C, 145D, close to 154D, and 155A. Midrib: More green and lighter than 147A. Lower surface: Dull. Background: More green and darker than 147B. Chevrons: 146B, 146C, 146D, 144A, 144B, 144C, and 155A. Midrib: Close to 146B. Petiole: Length: About 30 cm. Diameter, at base: About 1.6 cm. Diameter, just above wing: About 1.2 cm. Diameter, just below leaf: About 8 mm. Length of wing: About 7 cm. Width of wing: About 4 mm. Color: Close to 146A.

Inflorescence description: Inflorescence development has not been observed on plants of the new Dieffenbachia grown under typical shade house conditions.

Disease resistance: Resistance to pathogens common to Dieffenbachia has not been observed on plants of the new Dieffenbachia to date.

It is claimed:

1. A new and distinct cultivar of Dieffenbachia plant named 'Bryant Compacta', as illustrated and described.

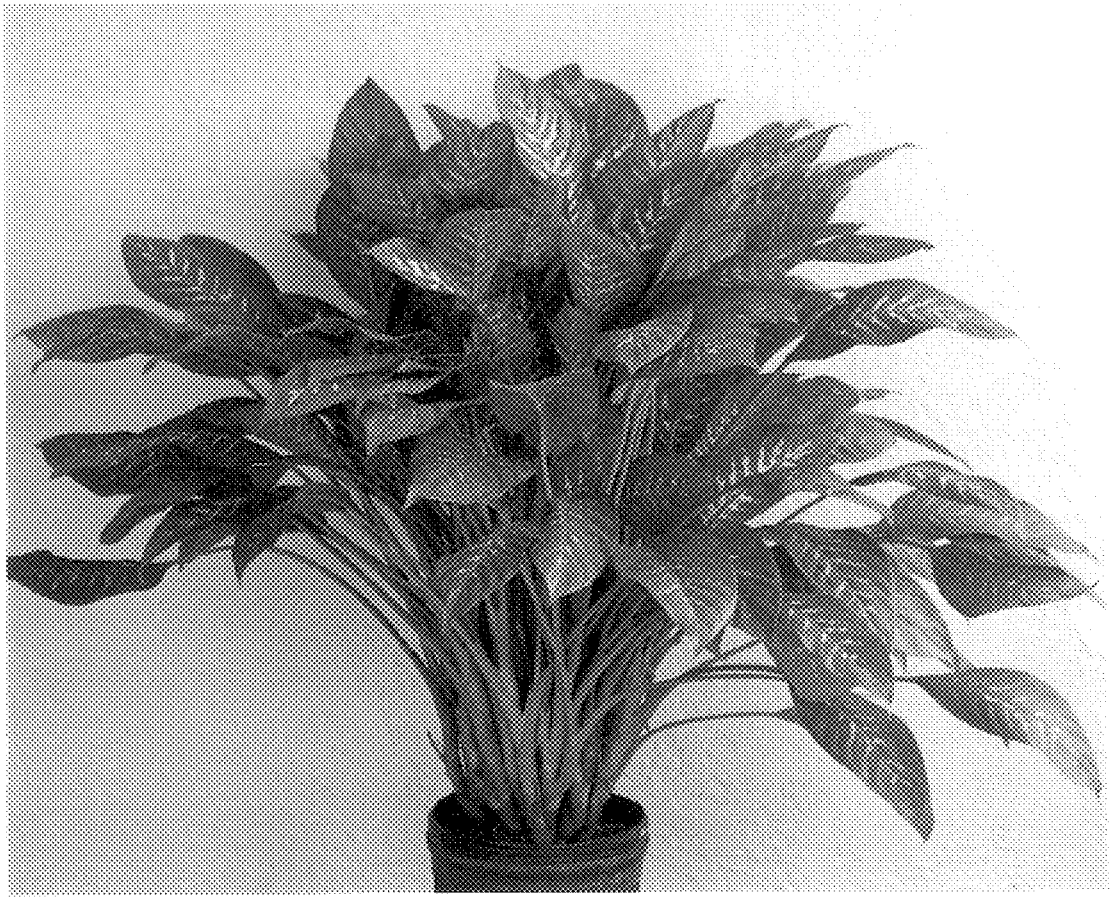

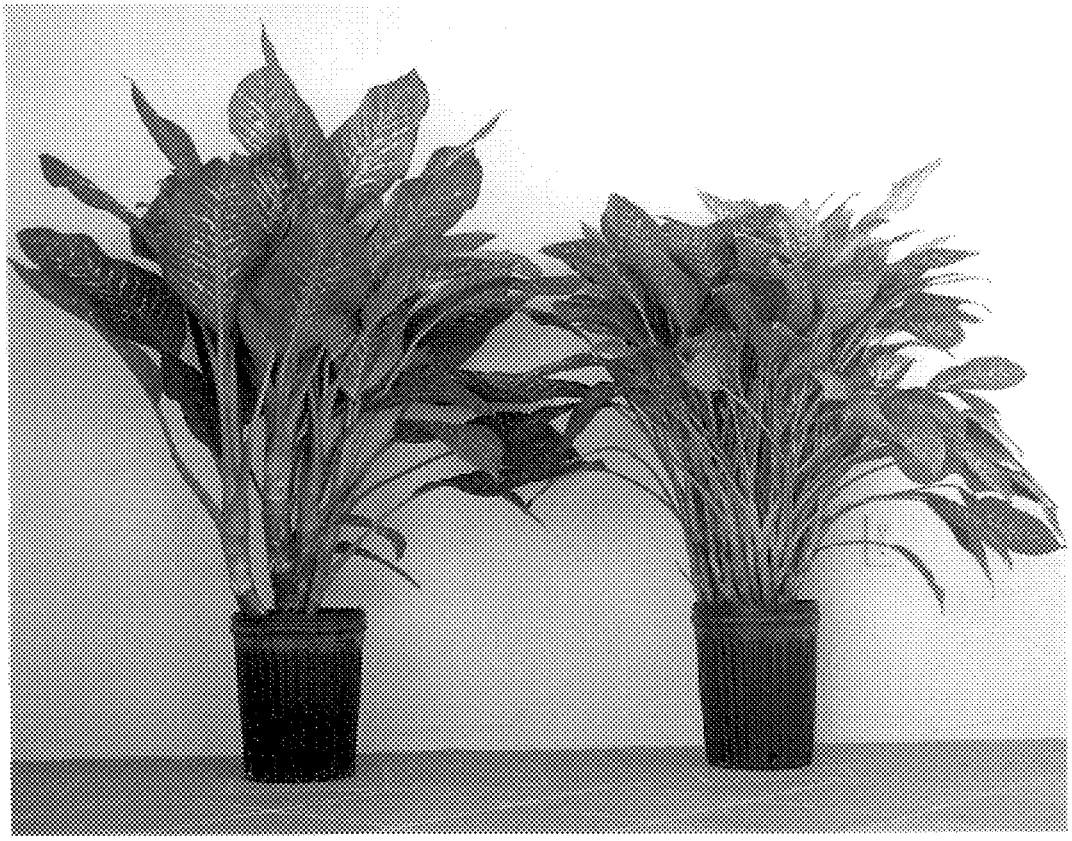

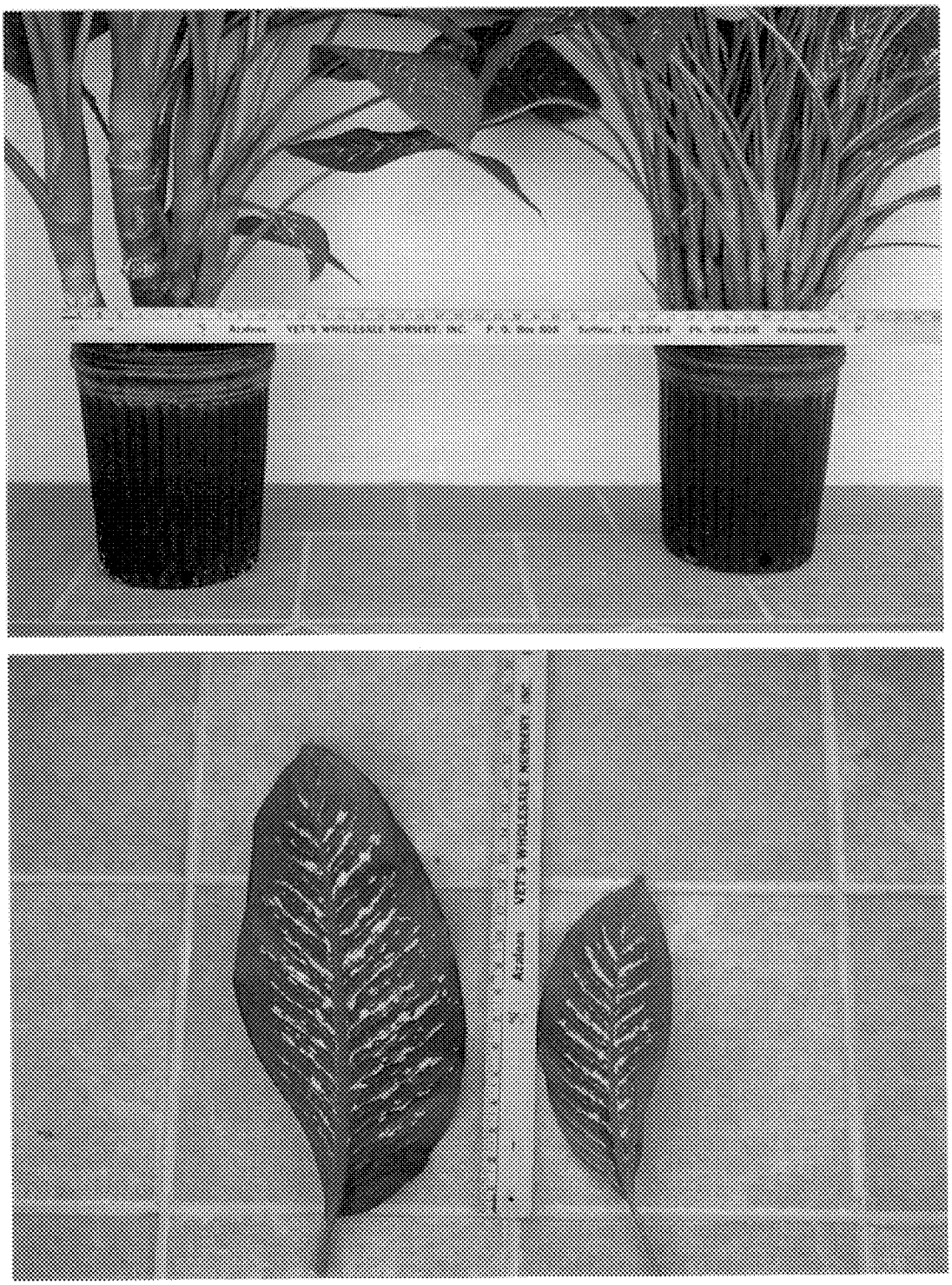

* * * * *